(12) United States Patent
Sun et al.

(10) Patent No.: US 9,612,187 B1
(45) Date of Patent: Apr. 4, 2017

(54) EXPERIMENTAL APPARATUS FOR STUDYING GAS INVASION AND MIGRATION MECHANISM IN OIL AND GAS WELLBORES

(71) Applicant: China University of Petroleum (East China), Qingdao, Shandong (CN)

(72) Inventors: Baojiang Sun, Shandong (CN); Yanli Guo, Shandong (CN); Hao Li, Shandong (CN); Linsong Song, Shandong (CN)

(73) Assignee: China University of Petroleum (East China), Shandong (CN)

( * ) Notice: Subject to any disclaimer, the term of this patent is extended or adjusted under 35 U.S.C. 154(b) by 0 days.

(21) Appl. No.: 15/293,006

(22) Filed: Oct. 13, 2016

(30) Foreign Application Priority Data

Sep. 8, 2016 (CN) .......................... 2016 1 0810406

(51) Int. Cl.
  *G01N 15/08* (2006.01)
  *E21B 47/10* (2012.01)
  *G01N 13/00* (2006.01)
(52) U.S. Cl.
  CPC ......... *G01N 15/0826* (2013.01); *E21B 47/10* (2013.01); *G01N 13/00* (2013.01); *G01N 15/082* (2013.01)
(58) Field of Classification Search
  CPC .. G01N 15/0826; G01N 15/082; G01N 13/00; E21B 47/10
  See application file for complete search history.

(56) References Cited

U.S. PATENT DOCUMENTS

| | | | | |
|---|---|---|---|---|
| 4,283,128 A | * | 8/1981 | Meyer | ............... G01N 15/0227 250/301 |
| 5,263,360 A | * | 11/1993 | Blauch | ..................... C09K 8/58 166/250.02 |
| 7,303,011 B2 | * | 12/2007 | Reid | ....................... E21B 49/04 166/100 |
| 2008/0265654 A1 | * | 10/2008 | Kearl | .................. E21B 43/2401 299/14 |

\* cited by examiner

*Primary Examiner* — Paul West
(74) *Attorney, Agent, or Firm* — Calfee, Halter & Griswold LLP

(57) ABSTRACT

The present invention provides an experimental apparatus for studying the gas invasion and migration mechanism in oil and gas wellbores, comprising: a wellbore; a wellbore pressure control unit, configured to control the pressure in the wellbore; a drilling fluid injection and discharge unit, configured to control the volume of a drilling fluid in the wellbore; a temperature control unit, configured to control the temperature in the wellbore; a rock core clamper, configured to clamp a rock core in a way that one side of the rock core is exposed to the drilling fluid in the wellbore; a gas invasion unit, configured to inject a gas into the rock core; and a measuring device, configured to measure the data related to one or more of the following items in the wellbore: gas bubble migration velocity, diffusion concentration and particle size distribution, gas bubble merging process, hydrate phase transition process, and migration velocity, diffusion concentration and particle size distribution of hydrate after phase transition.

9 Claims, 3 Drawing Sheets

EXPERIMENTAL APPARATUS FOR STUDYING GAS INVASION AND MIGRATION MECHANISM IN OIL AND GAS WELLBORES

CROSS REFERENCE TO RELATED APPLICATIONS

This application claims priority to Chinese Application No. 201610810406.5, filed on Sep. 8, 2016, entitled "Experimental Apparatus for Studying Gas Invasion and Migration Mechanism in Oil and Gas Wellbores", which is specifically and entirely incorporated by reference.

FIELD OF THE INVENTION

The present invention relates to the technical field of offshore drilling, particularly relates to an experimental apparatus for studying the gas invasion and migration mechanism in oil and gas wellbores, and especially relates to an experimental apparatus for studying the gas invasion and migration mechanism in deep water oil and gas wellbores during well shutdown.

BACKGROUND OF THE INVENTION

As onshore oil and gas resources are depleted gradually, the exploitation of offshore oil and gas resources has received more and more attention. Especially, deep-water oil and gas resources will be the key in exploration and exploitation, owing to their high reserve. Deep-water well drilling is different from shallow-water drilling and onshore drilling: the low-temperature and high-pressure deep-water environment, generation of hydrates, and existence of shallow gas sharply increase risk of gas kick and well blowout during deep-water well drilling and have strong impacts on the safety and time efficiency of the drilling operation; in deep sea areas, where high-permeability reservoir beds exist, gas kick may happen more easily, and more severe accidents may occur if the gas kick turns to well blowout. In the past, more attention was paid to the research on the mechanism of gas kick and the blowout control method in the well drilling process. Actually, in the process of drilling stop, waiting on cement, and well shutdown for protection against typhoon, etc., there is also a risk of gas invasion into the wellbore. For example, a well blowout and oil spill accident happened in the "Deepwater Horizon" oil rig in the Gulf of Mexico in 2010. Thus, it can be seen that gas kick prevention and control in different deep-water well drilling processes has become a major challenge to be solved in the exploitation of deep-water oil and gas resources. The mechanism of gas invasion into the wellbore and the gas bubble migration mechanism in the wellbore must be studied on the basis of the characteristics of gas kick to obtain a well kick control theory.

The mechanism of gas invasion and migration during shutdown of deep-water oil and gas well is difficult to accurately describe with the existing theory; in addition, most conventional experiments on the gas invasion and migration mechanism are made at normal temperature and normal pressure, and can't truly simulate deep-water environment and reservoir bed conditions. Hence, it is necessary to design an experimental apparatus that simulates the gas invasion and migration process during shutdown of a deep-water oil and gas well with reference to the wellbore temperature and pressure, and reservoir bed characteristics in deep-water, and use the experimental apparatus to study the mechanism of strata gas invasion into wellbores and the mechanism of gas bubble migration, merging and/or phase transition in wellbores, in order to provide an experimental basis for establishing a theoretical model of gas kick and thereby provide theoretical support for safe and efficient offshore deep-water well drilling.

SUMMARY OF THE INVENTION

The object of the present invention is to provide an experimental apparatus for studying the mechanism of gas invasion and migration in oil and gas wellbores, which can be used to study the mechanism of strata gas invasion into wellbores and the mechanism of gas bubble migration, merging and/or phase transition in wellbores, in order to provide an experimental basis for establishing a theoretical model of gas kick and thereby provide theoretical support for safe and efficient offshore deep-water well drilling.

To attain the object described above, in the embodiments of the present invention, an experimental apparatus for studying the gas invasion and migration mechanism in oil and gas wellbores is provided, comprising: a wellbore; a wellbore pressure control unit, configured to control the pressure in the wellbore; a drilling fluid injection and discharge unit, configured to control a volume of a drilling fluid in the wellbore; a temperature control unit, configured to control the temperature in the wellbore; a rock core clamper, configured to clamp a rock core in a way that one side of the rock core is exposed to the drilling fluid in the wellbore; a gas invasion unit, configured to inject a gas into the rock core; and a measuring device, configured to measure the data related to one or more of the following items in the wellbore: gas bubble migration velocity, diffusion concentration and particle size distribution, gas bubble merging process, hydrate phase transition process, and migration velocity, diffusion concentration and particle size distribution of hydrate after phase transition.

Optionally, the rock core clamper comprises: a top cover; a base, configured to accommodate the rock core, and having an lower end communicating with a piston chamber; and a piston being movable in the piston chamber, and configured to control the exposed area of the rock core to the drilling fluid in the wellbore.

Optionally, the piston is arranged with an expansion seal ring on its side wall, and the expansion seal ring is in contracted state when the piston moves up and down in the piston chamber, and is in expanded state after the piston moves to a preset position, to seal a part of the rock core that is not exposed to the drilling fluid.

Optionally, the piston is arranged with two expansion seal rings on its side wall, and the spacing between the two expansion seal rings is equal to the thickness of the rock core.

Optionally, the rock core clamper further comprises sealing gaskets configured to seal the upper end and the lower end of the rock core accommodated in the base.

Optionally, the temperature control unit comprises an upper wellbore temperature control unit and a lower wellbore temperature control unit, which are configured to control a temperature in an upper part of the wellbore and a temperature in a lower part of the wellbore respectively, so that the temperature in the lower part of the wellbore is higher than the temperature in the upper part of the wellbore, and the hydrate phase transition process happens only in the upper part of the wellbore.

Optionally, the wellbore comprises: an inner tube, an upper outer tube located around the upper side wall of the inner tube, and a lower outer tube located around the lower side wall of the inner tube.

Optionally, the upper wellbore temperature control unit and the lower wellbore temperature control unit comprise respectively: a liquid reservoir; an injection pump, configured to pump a liquid stored in the liquid reservoir to flow through the upper outer tube or the lower outer tube; and a temperature regulator, configured to regulate a liquid temperature in the upper outer tube or the liquid temperature in the lower outer tube.

Optionally, an upper part and a lower part of the wellbore are arranged with a sight window respectively, so that the information on gas bubble migration velocity, diffusion concentration and particle size distribution, and gas bubble merging process is measured through the sight window arranged on the lower part of the wellbore, and the information on the hydrate phase transition process and the hydrate migration velocity, diffusion concentration and particle size distribution after phase transition is measured through the sight window arranged on the upper part of the wellbore.

Optionally, the gas invasion unit comprises: a gas reservoir; and a constant-pressure and constant-flow micro-pump, configured to inject a gas stored in the gas reservoir into the rock core.

With the above-mentioned technical scheme, the wellbore temperature and pressure environment and the reservoir bed conditions in deep-water can be simulated, and experimental study on the mechanism of gas invasion into deep-water wellbores and the mechanism of gas bubble migration, merging, and phase transition in wellbores can be carried out, to reveal the rule of gas diffusion, displacement, migration, merging, and phase transition, and provide an experimental basis for establishing a theoretical model of gas kick in deep-water oil and gas well drilling that takes account of the coupling between strata and wellbore.

Other features and advantages of the present invention will be further detailed in the embodiments hereunder.

DESCRIPTION OF THE DRAWINGS

The accompanying drawings are provided here to facilitate further understanding on the present invention, and constitute a part of this document. They are used in conjunction with the following embodiments to explain the present invention, but shall not be comprehended as constituting any limitation to the present invention. Among the drawings.

| Description of the Symbols | | | |
|---|---|---|---|
| 11 | Inner tube | 12a | Lower outer tube |
| 12b | Upper outer tube | 13 | Sight window |
| 20 | Wellbore pressure control unit | 30 | Drilling fluid injection and discharge unit |
| 41 | Liquid reservoir | 42a | Lower injection pump |
| 42b | Upper injection pump | 43a | Lower temperature regulator |
| 43b | Upper temperature regulator | 44a | Lower injection pipeline |
| 44b | Upper injection pipeline | 45a | Lower discharge pipeline |
| 45b | Upper discharge pipeline | 46 | Temperature sensor |
| 50 | Rock core clamper | 51 | Top cover |
| 52 | Base | 53 | Piston chamber |
| 54 | Piston | 55 | Piston rod |
| 56a, 56b | Expansion seal ring | 57 | Threaded hole seat |
| 58a, 58b | Sealing gasket | 59 | Bearing |
| 61 | Gas reservoir | 62 | Constant-pressure and constant-flow micro-pump |
| 71 | Particle dynamics analyzer | 72 | High-speed camera system |
| 80 | Rock core | 90 | Hydraulic pipeline |

DETAILED DESCRIPTION OF THE EMBODIMENTS

Hereunder some embodiments of the present invention will be detailed with reference to the accompanying drawings. It should be appreciated that the embodiments described here are only provided to describe and explain the present invention, but shall not be deemed as constituting any limitation to the present invention.

Figure 1:
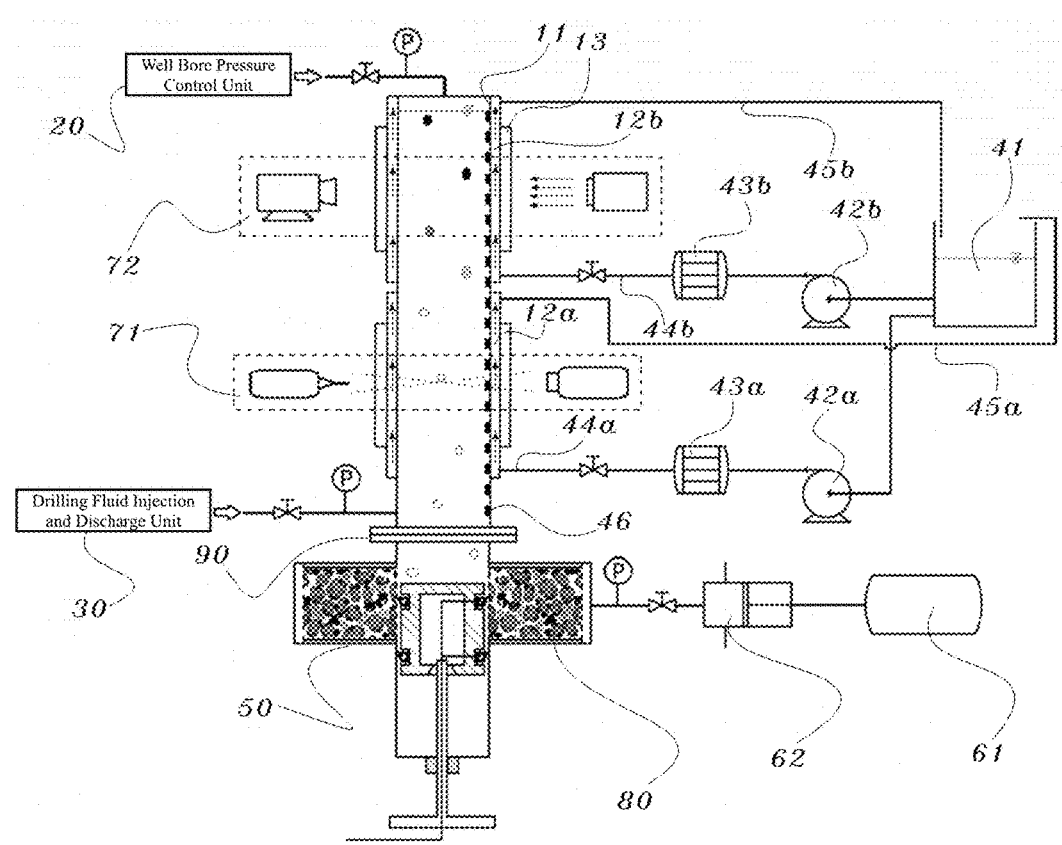
FIG. 1 is a schematic diagram of the experimental apparatus for studying the mechanism of gas invasion and migration in oil and gas wellbores according to an embodiment of the present invention.

FIG. 1 is a schematic diagram of the experimental apparatus for studying the mechanism of gas invasion and migration in oil and gas wellbores according to an embodiment of the present invention. As shown in FIG. 1, the experimental apparatus for studying the mechanism of gas invasion and migration in oil and gas wellbores provided in an embodiment of the present invention comprises: a wellbore; a wellbore pressure control unit 20, configured to control the pressure in the wellbore; a drilling fluid injection and discharge unit 30, configured to control the volume of a drilling fluid in the wellbore; a temperature control unit, configured to control the temperature in the wellbore; a rock core clamper 50, configured to clamp a rock core 80 in a way that one side of the rock core 80 is exposed to the drilling fluid in the wellbore; a gas invasion unit, configured to inject a gas into the rock core 80; and a measuring device, configured to measure the data related to one or more of the following items in the wellbore: gas bubble migration velocity, diffusion concentration and particle size distribution, gas bubble merging process, hydrate phase transition process, and migration velocity, diffusion concentration and particle size distribution of hydrate after phase transition. With the experimental apparatus, the wellbore temperature and pressure environment and the reservoir bed conditions in deep-water can be simulated, and experimental study on the mechanism of gas invasion into wellbores and the mechanism of gas bubble migration, merging, and phase transition in wellbores can be carried out, to reveal the rule of gas diffusion, displacement, migration, merging, and phase transition, and provide an experimental basis for establishing a theoretical model of gas kick in deep-water oil and gas well drilling that takes account of the coupling between strata and wellbore.

The wellbore pressure control unit 20 may be arranged on the top of the wellbore and control the pressure in the wellbore by injecting nitrogen into the wellbore. Certainly, the present invention is not limited to that. Other wellbore pressure control means are also applicable. For example, the drilling fluid injection and discharge unit can be used to regulate the volume of drilling fluid injected into the wellbore, thereby realizing wellbore pressure control.

The temperature control unit may comprise an upper wellbore temperature control unit and a lower wellbore temperature control unit, which are configured to control the temperature in the upper part of the wellbore and the temperature in the lower part of the wellbore respectively, so that the temperature in the lower part of the wellbore is higher than the temperature in the upper part of the wellbore, and the hydrate phase transition process happens only in the upper part of the wellbore. A particle dynamics analyzer 71 can be employed for the lower part of the wellbore to acquire gas bubble migration velocity, diffusion concentration and particle size distribution data (e.g., through a sight window arranged on the lower part of the wellbore), and a high-speed camera system 72 can be employed for the lower part of the wellbore to acquire information on the gas bubble merging process (e.g., through the sight window arranged on the lower part of the wellbore). A high-speed camera system 72 can be employed for the upper part of the wellbore to acquire information on the hydrate phase transition process (e.g., through a sight window 13 arranged on the upper part of the wellbore), and a particle dynamics analyzer 71 can be employed for the upper part of the wellbore to acquire the hydrate migration velocity, diffusion concentration and particle size distribution after phase transition (e.g., through the sight window 13 arranged on the upper part of the wellbore). The temperature control unit may be any apparatus that can control the temperature in the upper part of the wellbore and the temperature in the lower part of the wellbore. The embodiment shown in FIG. 1 is only a specific embodiment of the temperature control unit.

In the embodiment shown in FIG. 1, the wellbore comprises: an inner tube 11, an upper outer tube 12b located around the upper side wall of the inner tube 11, and a lower outer tube 12a located around the lower side wall of the inner tube 11. The temperature control unit comprises the upper wellbore temperature control unit and the lower wellbore temperature control unit, which may control the temperature in the upper part of the wellbore and the temperature in the lower part of the wellbore via the upper outer tube 12b and the lower outer tube 12a respectively. The upper wellbore temperature control unit and the lower wellbore temperature control unit consist of the same or similar components. Therefore, the structure of the lower wellbore temperature control unit will be described only hereunder. Reference can be made to FIG. 1 for the structure of the upper outer tube temperature control unit.

The lower wellbore temperature control unit comprises: a liquid reservoir 41; an injection pump 42, configured to pump the liquid stored in the liquid reservoir 41 to flow through the lower outer tube 12a; and a lower temperature regulator 43a, configured to regulate the liquid temperature in the lower outer tube 12a. The liquid at a regulated temperature is injected through a lower injection pipeline 44a via the lower outer tube 12a to transfer heat into the lower part of the wellbore, and then is discharged back to the liquid reservoir 41 through a lower discharge pipeline 45a. Thus, the temperature control in the lower part of the wellbore is realized. FIG. 1 further shows temperature sensors 46, which are evenly distributed on the inner wall of the wellbore to monitor the temperatures in each part of the wellbore, so that the temperature control unit can regulate the temperatures in each part of the wellbore on the basis of the monitoring result.

Figure 2:
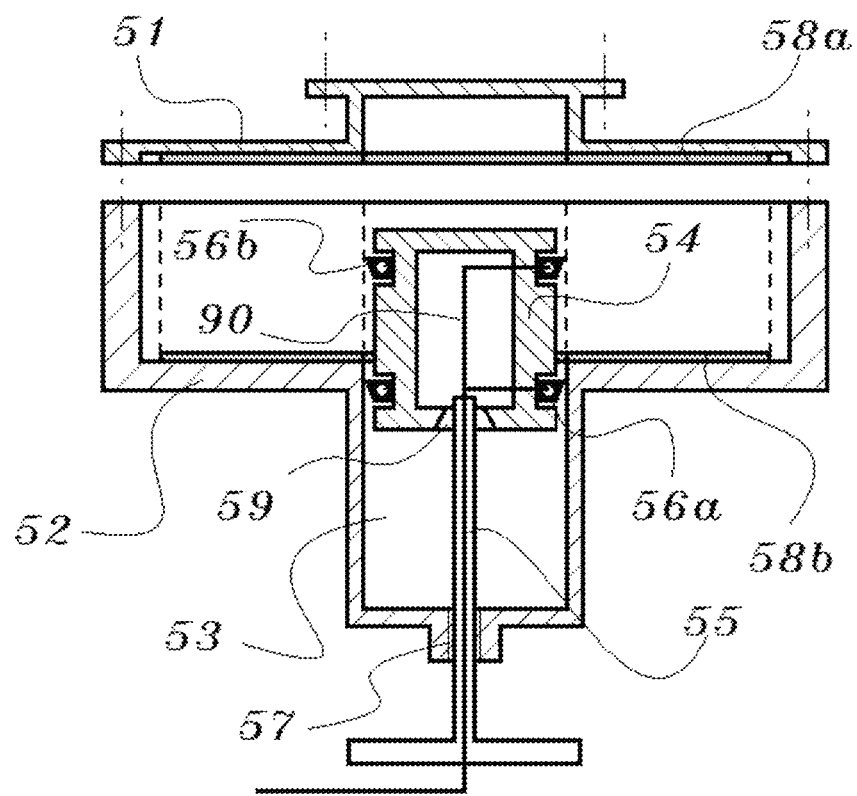
FIG. 2 is a schematic structural diagram of the rock core clamper.

The rock core clamper 50 is configured to clamp a rock core, and may be arranged on the bottom of the wellbore and communicate with the wellbore via a flange, so that one side of the rock core clamped by the rock core clamper 50 is exposed to the drilling fluid in the wellbore. FIG. 2 shows the structure of the rock core clamper. As shown in FIG. 2, the rock core clamper comprises: a top cover 51; a base 52, configured to accommodate the rock core and having an lower end communicating with a piston chamber 53; and a piston 54, being movable in the piston chamber 53, configured to control the exposed area of the rock core to the drilling fluid in the wellbore, to simulate different thicknesses of reservoir bed. The piston 54 may be driven by a piston rod 55 connected to the piston 54 by a mechanical drive means (e.g., as shown in FIG. 2, the piston rod 55 may be rotated by means of the coordination between a threaded hole seat 57 and a bearing 59, so that the piston 54 is moved), or may be hydraulically driven in direct.

Figure 3:
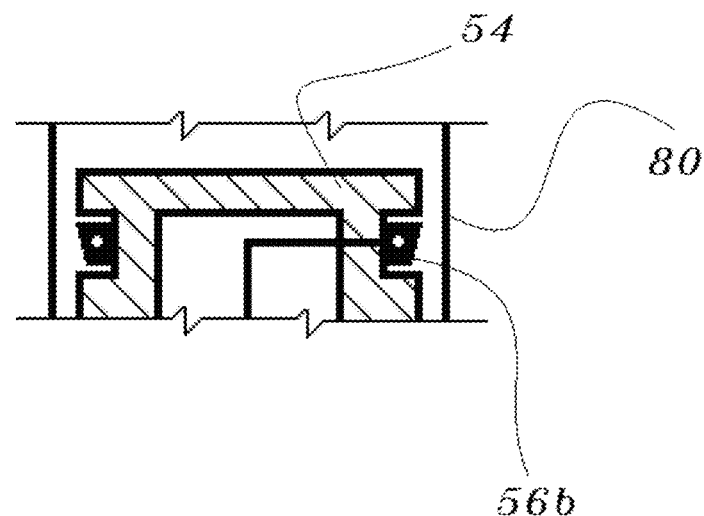
FIG. 3 is a schematic diagram of the rock core clamper when the expansion seal ring in the rock core clamper is in a contracted state.
Figure 4:
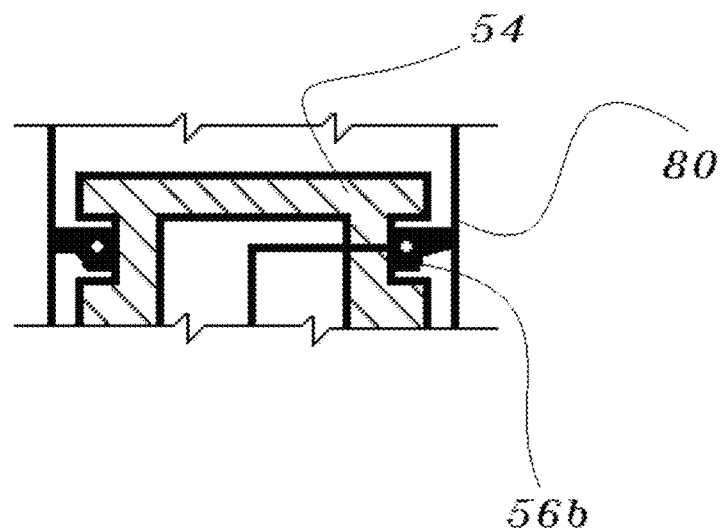
FIG. 4 is a schematic diagram of the rock core clamper when the expansion seal ring in the rock core clamper is in an expanded state.

Preferably, the piston 54 is arranged with expansion seal rings 56a and 56b on its side wall, and the expansion seal rings 56a and 56b are in contracted state when the piston 54 moves up and down in the piston chamber 53 (as shown in FIG. 3, the expansion seal rings 56a and 56b do not contact with the side wall of the rock core or do not closely contact with it), and are in expanded state after the piston 54 moves to a preset position (as shown in FIG. 4, the expansion seal rings 56a and 56b contact closely with the side wall of the rock core), to seal a part of the rock core that is not exposed to the drilling fluid. Thus, on one hand, the piston 54 can move smoothly in the piston chamber 53; on the other hand, the piston 54 is guaranteed in a leak-tight state towards the rock core. FIG. 2 shows the two expansion seal rings 56a and 56b, wherein, the spacing between the two expansion seal rings 56a and 56b is equal to the thickness of the rock core.

The expansion seal rings 56a and 56b can be made to expand by injecting hydraulic oil into them through a hydraulic pipeline 90, and can be made to contract by discharging the hydraulic oil from them through the hydraulic pipeline 90.

Preferably, the rock core clamper further comprises sealing gaskets 58a and 58b configured to seal the upper end and the lower end of the rock core accommodated in the base 52, to ensure the leak tightness of the rock core and prevent the gas injected into the rock core by the gas invasion unit from spilling.

The gas invasion unit comprises: a gas reservoir 61, configured to store a gas that is used to simulate gasses that may exist in the reservoir bed, such as paraffin gases, e.g., methane; and a constant-pressure and constant-flow micro-pump 62, configured to inject the gas stored in the gas reservoir 61 into the rock core, to keep the concentration of gas stored in the rock core and thereby simulate a true reservoir bed.

Certainly, as shown in FIG. 1, there are some valves and pressure meters; for example, a pressure meter and a valve are arranged between the constant-pressure and constant-flow micro-pump 62 and the rock core, a valve and a pressure meter are arranged between the drilling fluid injection and discharge unit 30 and the wellbore, and a valve and a pressure meter are arranged between the wellbore pressure control unit 20 and the wellbore. The functions of those valves and pressure meters are obvious, and will not be detailed here.

To carry out an experiment on the mechanism of gas invasion and migration during closing of deep-water oil and gas wellbore, firstly, porous media different in permeability are prepared according to the dimensions of the rock core clamper to simulate a real rock core; then, the rock core is loaded into the rock core clamper, the rock core clamper is connected to the wellbore, and the piston is adjusted to a preset position; a prepared drilling fluid is injected via the drilling fluid injection and discharge unit to the experimental wellbore; the pressure in the wellbore is set via the wellbore pressure control unit; the temperature range in the upper part of the wellbore and the temperature range in the bottom part of the wellbore are regulated via the upper wellbore temperature control unit and the lower wellbore temperature control unit to preset values respectively; a gas is injected at constant pressure and constant flow rate into the rock core clamper via the gas invasion unit, and the volume of the invading gas is measured; a gas bubble rising process mainly happens at the lower sight window, and the gas bubble migration velocity, diffusion concentration and particle size distribution of the invading gas may be measured with a particle dynamics analyzer, and the gas bubble merging process may be recorded with a high-speed camera; a hydrate phase transition and rising process mainly happens at the upper sight window, and the natural gas hydrate phase transition process may be recorded with a high-speed camera, and the hydrate migration velocity, diffusion concentration and particle size distribution after phase transition may be measured with a particle dynamics analyzer.

The apparatus provided in the present invention can simulate a wellbore temperature and pressure environment and reservoir bed conditions in deep-water, and can be used to carry out experimental study on strata gas invasion into wellbores under different uncovered reservoir thickness, different reservoir pressure, and different gas invasion volume conditions in deep-water well drilling, real-time measure gas bubble rising velocity, diffusion concentration and particle size distribution in wellbores, and carry out experimental study on the gas bubble merging mechanism and the natural gas hydrate phase transition mechanism. The experimental apparatus for studying the gas invasion and migration mechanism provided in the present invention is simple in structure and easy to implement, employs a scientific parameter measurement method, and has high feasibility and measurement accuracy.

While some preferred embodiments of the present invention are described above with reference to the accompanying drawings, the present invention is not limited to the details in those embodiments. Those skilled in the art can make modifications and variations to the technical scheme of the present invention, without departing from the spirit of the present invention. However, all these modifications and variations shall be deemed as falling into the protected scope of the present invention.

In addition, it should be appreciated that the technical features described in the above embodiments can be combined in any appropriate manner, provided that there is no conflict among the technical features in the combination. To avoid unnecessary iteration, such possible combinations are not described here in the present invention.

Those skilled in the art can appreciate that all or a part of the steps constituting the method in the above-mentioned embodiment can be implemented by instructing relevant hardware with a program, which is stored in a storage medium and includes several instructions to instruct a single-chip microcomputer, a chipset, or a processor to execute all or a part of the steps of the methods in the embodiments of the present application. The storage medium comprises: U-disk, removable hard disk, Read-Only Memory (ROM), Random Access Memory (RAM), diskette, or CD-ROM, or a similar medium that can store program codes.

Moreover, different embodiments of the present invention can be combined freely as required, as long as the combinations don't deviate from the ideal and spirit of the present invention. However, such combinations shall also be deemed as falling into the scope disclosed in the present invention.

What is claimed is:

1. An experimental apparatus for studying the gas invasion and migration mechanism in oil and gas wellbores, comprising:
    a wellbore;
    a wellbore pressure control unit, configured to control the pressure in the wellbore;
    a drilling fluid injection and discharge unit, configured to control a volume of a drilling fluid in the wellbore;
    a temperature control unit, configured to control the temperature in the wellbore;
    a rock core clamper, configured to clamp a rock core in a way that one side of the rock core is exposed to the drilling fluid in the wellbore, wherein the rock core clamper comprises:
        a top cover;
        a base, configured to accommodate the rock core, and having an lower end communicating with a piston chamber; and
        a piston being movable in the piston chamber, and configured to control the exposed area of the rock core to the drilling fluid in the wellbore;
    a gas invasion unit, configured to inject a gas into the rock core; and
    a measuring device, configured to measure the data related to one or more of the following items in the wellbore:
        gas bubble migration velocity,
        gas bubble diffusion concentration,
        gas bubble particle size distribution,
        gas bubble merging process,
        hydrate phase transition process,
        hydrate migration velocity after the phase transition,
        hydrate diffusion concentration after the phase transition, and
        hydrate particle size distribution after the phase transition.

2. The experimental apparatus according to claim 1, wherein the piston is arranged with an expansion seal ring on its side wall, and the expansion seal ring is in contracted state when the piston moves up and down in the piston chamber, and is in expanded state after the piston moves to a preset position, to seal a part of the rock core that is not exposed to the drilling fluid.

3. The experimental apparatus according to claim 2, wherein the piston is arranged with two expansion seal rings on its side wall, and the spacing between the two expansion seal rings is equal to the thickness of the rock core.

4. The experimental apparatus according to claim 1, wherein the rock core clamper further comprises sealing gaskets configured to seal the upper end and the lower end of the rock core accommodated in the base.

5. The experimental apparatus according to claim 1, wherein the temperature control unit comprises an upper wellbore temperature control unit and a lower wellbore temperature control unit, which are configured to control a temperature in an upper part of the wellbore and a temperature in an lower part of the wellbore respectively, so that the temperature in the lower part of the wellbore is higher than the temperature in the upper part of the wellbore, and the hydrate phase transition process happens only in the upper part of the wellbore.

6. The experimental apparatus according to claim 5, wherein the wellbore comprises: an inner tube, an upper outer tube located around the upper side wall of the inner tube, and a lower outer tube located around the lower side wall of the inner tube.

7. The experimental apparatus according to claim 6, wherein the upper wellbore temperature control unit and the lower wellbore temperature control unit comprise respectively:
   a liquid reservoir;
   an injection pump, configured to pump a liquid stored in the liquid reservoir to flow through the upper outer tube or the lower outer tube; and
   a temperature regulator, configured to regulate a liquid temperature in the upper outer tube or the liquid temperature in the lower outer tube.

8. The experimental apparatus according to claim 1, wherein an upper part and a lower part of the wellbore are arranged with a sight window respectively, so that the information on the gas bubble migration velocity, the gas bubble diffusion concentration, and the gas bubble particle size distribution, and the gas bubble merging process is measured through the sight window arranged on the lower part of the wellbore, and the information on the hydrate phase transition process, the hydrate migration velocity after the phase transition, the hydrate diffusion concentration after the phase transition, and the hydrate particle size distribution after the phase transition is measured through the sight window arranged on the upper part of the wellbore.

9. The experimental apparatus according to claim 1, wherein the gas invasion unit comprises:
   a gas reservoir; and
   a constant-pressure and constant-flow micro-pump, configured to inject a gas stored in the gas reservoir into the rock core.

* * * * *